US009095640B2

(12) United States Patent
Jennissen et al.

(10) Patent No.: US 9,095,640 B2
(45) Date of Patent: Aug. 4, 2015

(54) BIOACTIVE IMPLANT AND METHOD OF USE

(75) Inventors: Herbert P. Jennissen, Essen (DE);
Maria Chatzinikolaidou, Essen (DE);
Heike Rumpf, Marl (DE)

(73) Assignee: Morphoplant GMBH, Bochum (DE)

( * ) Notice: Subject to any disclaimer, the term of this patent is extended or adjusted under 35 U.S.C. 154(b) by 1092 days.

(21) Appl. No.: 12/135,077

(22) Filed: Jun. 6, 2008

(65) Prior Publication Data

US 2008/0260799 A1    Oct. 23, 2008

Related U.S. Application Data

(63) Continuation of application No. 10/343,520, filed as application No. PCT/DE01/02893 on Aug. 1, 2001, now abandoned.

(30) Foreign Application Priority Data

Aug. 1, 2000   (DE) ................................. 100 37 850

(51) Int. Cl.
*A61F 2/00*      (2006.01)
*A61L 27/22*     (2006.01)
*A61L 27/54*     (2006.01)
*A61L 31/08*     (2006.01)
*A61L 27/28*     (2006.01)
*A61L 27/50*     (2006.01)
*A61L 31/10*     (2006.01)

(52) U.S. Cl.
CPC ............... *A61L 27/227* (2013.01); *A61L 27/54* (2013.01); *A61L 27/28* (2013.01); *A61L 27/50* (2013.01); *A61L 31/08* (2013.01); *A61L 31/10* (2013.01); *A61L 2300/406* (2013.01); *A61L 2300/414* (2013.01); *A61L 2300/802* (2013.01)

(58) Field of Classification Search
CPC ......... A61L 27/28; A61L 27/50; A61L 31/08; A61L 31/10
USPC ........ 424/423; 435/176; 514/2; 530/402, 811
See application file for complete search history.

(56) References Cited

U.S. PATENT DOCUMENTS

| | | | |
|---|---|---|---|
| 2,375,210 A | 5/1945 | Batcheller | |
| 4,002,602 A | 1/1977 | Goldstein | |
| 4,190,647 A | 2/1980 | Goldstein et al. | |
| 4,371,612 A | 2/1983 | Matsumoto et al. | |
| 4,652,459 A | 3/1987 | Engelhardt | |
| 4,828,563 A | 5/1989 | Muller-Lierheim | |
| 5,306,307 A | 4/1994 | Senter et al. | |
| 5,330,911 A | 7/1994 | Hubbell et al. | |
| 5,336,465 A * | 8/1994 | Matsunaga et al. ............... | 419/2 |
| 5,607,475 A | 3/1997 | Cahalan et al. | |
| 5,837,235 A | 11/1998 | Mueller et al. | |
| 5,876,454 A | 3/1999 | Nanci et al. | |
| 6,033,719 A | 3/2000 | Keogh | |
| 6,635,269 B1 | 10/2003 | Jennisson | |
| 2008/0260799 A1 | 10/2008 | Jennissen et al. | |

FOREIGN PATENT DOCUMENTS

| | | |
|---|---|---|
| CA | 2162114 | 11/1994 |
| CA | 2245683 | 8/1997 |
| DE | 324 15 89 | 5/1984 |
| DE | 195 48 476 | 6/1997 |
| DE | 197 13 213 | 10/1998 |
| DE | 198 18 098 | 11/1999 |
| DE | 197 55 801 | 6/2000 |
| EP | 0109061 | 5/1984 |
| EP | 0415845 | 3/1991 |
| GB | 387806 | 2/1933 |
| GB | 593287 | 10/1947 |
| WO | WO 90/09798 | 9/1990 |
| WO | WO 92/00047 | 1/1992 |
| WO | WO 94/26321 | 11/1994 |
| WO | WO 97/27821 | 8/1997 |
| WO | WO 99/26674 | 6/1999 |
| WO | WO 00/25841 | 5/2000 |
| WO | WO 02/09788 | 2/2002 |

OTHER PUBLICATIONS

Jennissen et al., "Biocoating of Implants with Mediator Molecules: Surface Enhancements of Metals by Treatment with Chromosulfuric Acid", 1999, Materialwissenschaft.und Werkstofftech, v. 30 No. 12, pp. 838-845.*
Jennissen et al., Biocoating of implants with mediator molecules: Surface enhancement of metals by treatment with chromosulfuric acid. Materialwissenschaft.und Werkstofftech, 30(12): 838-845, 1999.
International Search Report for PCT Application No. PCT/DE98/03463.
US Office Action dated Jan. 23, 2007 in U.S. Appl. No. 10/343,520.
US Office Action dated Jul. 27, 2007 in U.S. Appl. No. 10/343,520.
Andrade et al., "Effects of Plasma Protein Adsorption on Protein Conformation and Activity," *Pure Appl. Chem.*, 1984, vol. 56, pp. 1345-1350.
Chatzinikolaidou et al. "Biocoating of Electropolished and Ultra-Hydrophilic Titanium and Cobalt Chromium Molybdenium Alloy Surfaces with Proteins," *Mater. Sci. Eng. Technol.*, 2002, vol. 33, pp. 720-727.
Chatzinikolaidou et al., "Stability of Surface-Enhanced Ultrahydrophilic Metals as a Basis for Bioactive rhBMP-2 Surfaces," *Mater. Sci. Eng. Technol.*, 2003, vol. 34, pp. 1106-1112.

(Continued)

*Primary Examiner* — Ali Soroush
(74) *Attorney, Agent, or Firm* — Sheppard Mullin Richter & Hampton LLP

(57) ABSTRACT

The invention relates to a method for producing bioactive implant surfaces consisting of metallic or ceramic materials, to be used for implants such as artificial joints or very small implants such as so-called stents. The invention also relates to implants produced according to this method and methods of using the implants.

20 Claims, No Drawings

(56) References Cited

OTHER PUBLICATIONS

Chatzinikolaidou et al. "Peri-Implant Reactivity and Osteoinductive Potential of Immobilized rhBMP-2 on Titanium Carriers," *Acta Biomater.*, 2010, vol. 6, pp. 4405-4421.

Engel et al., "Kinetic and Structural Characterization of Adsorption-Induced Unfolding of Bovine a-Lactalbumin," *J. Biol. Chem.*, 2002, vol. 277, pp. 10922-10930.

Ito et al., "Patterned Artificial Juxtacrine Stimulation of Cells by Covalently Immobilized Insulin," *FEBS Lett.*, 1997, vol. 403, pp. 159-162.

Lahiri et al., "A Strategy for the Generation of Surfaces Presenting Ligands for Studies of Binding Based on an Active Ester as a Common Reactive Intermediate: A Surface Plasmon Resonance Study," *Anal. Chem.*, 1999, vol. 71, pp. 777-790.

Nakanishi et al., "On the Adsorption of Proteins on Solid Surfaces, a Common But Very Complicated Phenomenon," *J. Biosci. Bioeng.*, 2001, vol. 91, pp. 233-244.

Norde et al., "Structure of Adsorbed and Desorbed Proteins," *Colloid. Surf.*, 1991, vol. 64, pp. 87-93.

\* cited by examiner

BIOACTIVE IMPLANT AND METHOD OF USE

The present invention relates to a process for the production of bioactive implant surfaces of metallic or ceramic materials which are used for implants such as artificial joints, dental implants or alternatively very small implants, e.g. "stents", and to implants produced by the process, which, as an "active device", permit a controlled release of the bioactive molecules from the implant materials.

The implantation of artificial joints or bones has gained increasing importance in recent years, e.g. in the treatment of arthrodysplasia or joint luxation or in diseases which can develop on the wear of joints as a result of malarticulation. The function of the implants and the materials used for their production, which in addition to metals such as titanium or metal alloys can also include ceramics or plastic materials such as Teflon, have continually been improved such that implants can have service lives of 10 years in 90-95% of cases after a successful course of healing. Regardless of these advances and improved operative procedures, an implantation still remains a difficult and irksome intervention, in particular since it is associated with a prolonged healing process of the implant, which often comprises stays for months in clinics and health resorts including rehabilitation measures. In addition to the pain, the length of the treatment period and separation from the familiar environment are great burdens here for the patients affected. Furthermore, the prolonged healing process causes high personnel and care costs due to the intensive care being necessary.

The understanding of the processes at the molecular level which are necessary for successful ingrowth of an implant has expanded significantly in recent years. Structural compatibility and surface compatibility are crucial for the tissue compatibility of an implant. Biocompatibility in the narrower sense is limited solely by the surface. At all levels of integration, proteins play a decisive role. As explained below, they decide about the further course of the implant healing even during the implantation operation due to the formation of an initial adsorbed protein layer, since the first cells later settle on this layer.

In the molecular interaction between implant, which is also designated as a biomaterial, and tissue, a large number of reactions take place which appear to be strictly hierarchically ordered. As the first biological reaction, the adsorption of proteins on the surface of the biomaterial takes place. In the protein layer resulting thereby, subsequently individual protein molecules are converted, for example either by means of conformational changes to give signal substances which are presented on the surface, or protein fragments acting as signal substances are released by means of catalytic (proteolytic) reactions. Triggered by the signal substances, in the next phase cell population takes place, which can include a multiplicity of cells such as leucocytes, macrophages, immunocytes, and finally also tissue cells (fibroblasts, fibrocysts, osteoblasts, osteocytes). In this phase, other signal substances, "mediators", such as, for example, cytokines, chemokines, morphogens, tissue hormones and true hormones play a crucial role. In the case of biocompatibility, integration of the implant into the entire organism takes place, and ideally a permanent implant is obtained.

In the light of studies which have been carried out in recent years at the molecular level of osteogenesis, chemical signal substances, the "bone morphogenic proteins" (BMP-1-BMP-14), which have an influence on bone growth, have gained increasing importance. BMPs (in particular BMP-2 and BMP-4, BMP-5, BMP-6, BMP-7) are osteoinductive proteins, which stimulate bone regeneration and healing of the bone by bringing about the proliferation and differentiation of precursor cells to osteoblasts. Moreover, they promote the formation of alkaline phosphatase, hormone receptors, bone-specific substances such as collagen type 1, osteocalcin, osteopontin and finally mineralization. The BMP molecules in this case regulate the three key reactions chemotaxis, mitosis and differentiation of the respective precursor cell. Moreover, BMPs play an important role in embryogenesis, organogenesis of the bone and other tissue, known target cells being osteoblasts, chondroblasts, myoblasts and vascular smooth muscle cells (inhibition of proliferation by BMP-2).

14 BMPs including multiple isoforms are now known. Except for BMP-1, the BMPs belong to the "transforming growth factor beta" (TGF-) superfamily, for which specific receptors have been detected on the surfaces of the corresponding cells. As the successful employment of recombinant human BMP-2 and/or BMP-7 in experiments relative to defect healing processes in rats, dogs, rabbits and monkeys has shown, no species specificity appears to be present. Previous experiments to utilize the bone formation-inducing properties of the BMPs specifically for implantation purposes by applying BMP-2 and/or BMP-7 noncovalently to metallic or ceramic biomaterials have, however, very largely proceeded unsuccessfully.

The object of the present invention consists in making available improved biomaterials for use as implants, which are distinguished by an increased loading density with mediator molecules, in particular BMPs, and a prolonged long-term release into the tissue surrounding the implants.

According to the invention, this object is achieved by a process for the production of bioactive implant surfaces of metallic or ceramic materials being made available in which in a first step anchor molecules having hydrophobic radicals are covalently bonded to the surface of the implant material and in a second step mediator molecules which, as a result of noncovalent interactions between the mediator molecules and the hydrophobic radicals of the anchor molecules, are immobilized, are added to the implant material treated in this way, where in the first step the loading density of the anchor molecules on the implant surface is chosen, depending on the chain length of the hydrophobic radical of the anchor molecule, such that the anchor molecules do not interact with one another themselves and, depending on the covered surface on the implant material, which is covered by an individual mediator molecule absorbed in the second step, at least 10, preferably 15, contact sites are formed between the hydrophobic radicals of the anchor molecules for hydrophobic interaction with the mediator molecule.

The undesired interaction between the anchor molecules is primarily to be understood as meaning a steric interaction, which is not desired here, in order that the anchor molecules can interact with the mediator molecules in a manner which is sterically unhindered by one another.

Contact site is to be understood according to the invention as meaning the site of the greatest hydrophobic interaction between a radical of the anchor molecules and the mediator molecule. In this case, a number of contact sites can be present on one radical due to branching of the radical. Thus, a carbon chain terminally substituted by a methyl group can have at least two contact sites. The inventors have recognized that the immobilization of the mediator molecules by hydrophobic interaction depends crucially on the number of the contact sites for the hydrophobic interaction between the radicals and the mediator molecule. In this case, adjacent contact sites which are as close as possible are advantageous, so that more strongly branched radicals are preferred, since a number of adjacent contact sites are available here. For example, a terminal trimethyl group on a hydrophobic radical is preferred compared with a straight-chain unbranched chain having the same total number of carbon atoms.

In the immobilization process according to the invention, a degree of substitution of the anchor molecule is in particular achieved, therewith indirectly (i.e. surface concentration of the immobilized protein), which permits a multivalent interaction between surface and cell and makes it possible effectively to control bone or tissue formation.

In the process according to the invention, in a first step alkyl, alkenyl or alkynyl or aryl radicals having 1 to 30, preferably 3 to 20, particularly preferably 3 to 8, carbon atoms, which can also be replaced by silicon in the alkyl chain and/or heteroatoms such as N, O or S in the alkyl chain and/or in the aryl ring, preferably in a branched chain, which can also optionally be substituted by one or more substituents from halogen, alkoxy, hydroxyl, thiol, amino, alkyl- or dialkylamino groups, where the alkyl groups of the substituent preferably have 1-6 carbon atoms and can be straight-chain or branched, but are preferably unsubstituted and particularly preferably branched, are preferably covalently bonded to the surface of the implant material. This bonding of the radicals can in each case take place by means of a coupling via a silyl group, a bromocyano group or an amino group, for example of an aminoalkane.

In a second step, mediator molecules such as bone growth factors can be immobilized on the implant material by means of noncovalent bonding, presumably on account of hydrophobic interactions on the implant material. It is thereby made possible to form a chemotactically acting and/or biologically active, "juxtacrine", implant surface, which leads to the colonization, proliferation and differentiation of bone cells. Thus, "active implants" can be made available which in the case of molecules released from the surface show a chemotactic action on cells, in the case of BMPs on osteoblasts, at a distance of 500 to 1000 μm.

The determination of the loading density of the implant surface with anchor molecules, which as a rule only have one hydrophobic radical with, depending on the degree of branching, at least one contact site, is as a rule carried out starting from the size estimation of the mediator molecule, which is usually present as an ellipsoid. Subsequently, after perusal of the surface area of the mediator molecule projected onto the implant surface, the number of necessary contact sites is determined as at least 10 and, as a function thereof, the chain length and the degree of branching of the anchor molecules is established. The loading density is then calculated from this.

Initial investigations of the inventors showed that after modification of titanium surfaces with amino-propylsilane (APS), the number of immobilized amino groups determined using the Bolton-Hunter reagent showed values in the range from 1.0-2.5 nmol/cm$^2$. Taking into consideration Loschmidt's number, about 60 molecules/10 nm$^2$ result at 1 nmol/cm$^2$. From this value, a mean distance of the APS molecules from one another of about 0.4-0.5 nm can be calculated, which appears to be a reasonable value.

In the case of the coupling of the protein ubiquitin (m=8.5 kDa), the inventors obtained maximum values of 1-2 g/cm$^2$. On calculation using 1 g/cm$^2$, 3.85×10-11 mol/cm$^2$ are obtained. The conversion to molecules then gives 2.3 molecules of ubiquitin per 10 nm$^2$, thus a mean distance of the molecules with the assumption of a point size of 6.7 nm, which in the case of an estimated actual size of 3-4 nm diameter for the ubiquitin molecule means a quite high packing density in the form presumably of a monolayer on the surface. Since in the case of the adsorption of ubiquitin similarly high values (as in the case of the coupling of BMP-2) in the range from 1-3 g/cm$^2$ (=2-6 mol of ubiquitin/10 nm$^2$) are obtained, the inventors were able to calculate that on average to one molecule of ubiquitin 10-30 molecules APS (60/6 and 60/2) are available for an interaction reaction. The inventors were thus able to estimate that one molecule of ubiquitin covers an area ("footprint") which contains approximately this number of APS molecules, i.e. at most 10-30 APS molecules can theoretically react with one molecule of ubiquitin, where a random reaction is to be assumed.

With the assumption of a hydrophobic adsorption, according to determination of the inventors not all (i.e. 30) propyl radicals can react with the ubiquitin, since it does not have so many "hydrophobic patches" for a geometrically defined bond on one side of the molecule. According to estimation of the inventors, at most 4-10 alkyl radicals on the ubiquitin are therefore able to find a specific binding site and actually lead to the adsorption of ubiquitin.

If the degree of substitution is now reduced, i.e. the number of alkyl radicals/10 nm$^2$, the distance becomes so great that sufficient radicals can no longer react with the ubiquitin, and adsorption no longer takes place. On the other hand, if the alkyl chain length is increased, the binding energy of an alkyl chain with the protein is increased, and only a few alkyl radicals are needed in order to bind a molecule of ubiquitin.

When using BMP-2 (m=26 kDa) having a size of about 4×4×8 nm (bonding to longitudinal side), the inventors initially assumed a maximum occupation of approximately 0.5-1 molecule per 10 nm$^2$. This means that for BMP-2 on the basis of an approximately twice as large "footprint" only approximately half the number of the molecules are absorbed, BMP-2 instead also can cover approximately twice as many immobilized alkyl radicals (20-50), of which also, in turn, according to calculation of the inventors, presumably only at most 8-20 are available sterically for interactions with the BMP-2.

From experiments of the inventors with hexylagaroses which have only approximately 7-8 alkyl radicals/10 nm$^2$, it is known to them that an adsorption of BMP-2 is not possible with this low number of interaction partners. Experiments of the inventors have therefore shown that only in a higher range from about 10-60 alkyl radicals/10 nm$^2$ at a calculated distance of the radicals of 0.5-3 nm is a satisfactory adsorption of BMP-2 possible. An adsorption with a half-life of release of 90-100 days is, according to the knowledge of the inventors, only possible if a number of at least 8-15 alkyl radicals per BMP-2 molecule can be available for the reaction at specific sites. This interaction will, however, probably only be poor statistically according to calculation of the inventors at a degree of substitution of below 10 alkyl radicals/10 nm$^2$, such that higher degrees of substitution are more promising.

On the part of the inventors, it was found that a dependence of the chain length of the alkyl radicals employed and of the distance of the alkyl radicals from one another for the best-possible adsorption of mediator molecules exists. On the one hand, the length of the chains must not be so large that the radicals are tangled together on the implant surface, on the other hand the distance of the radicals to one another must be so great that these do not interact with one another. Depending on the size of the absorbed mediator molecule, best-possible values for the occupation of the surface of the implant with respect to the chain length, the degree of branching of the chain and the distance of the radicals thus result for the individual case. For the adsorption of the BMP-2, the inventors have determined an occupation of 10 to 60 radicals per 10 nm$^2$, preferably 10 to 30 radicals per 10 nm$^2$, at a chain length of between 1 to 30, preferably 1 to 20, particularly preferably 1 to 8, carbon atoms, preferably in a chain which can also optionally be substituted by one or more substituents from halogen, alkoxy, hydroxyl, thiol, amino, alkyl or dialkylamino groups.

In a preferred variant, to increase the interaction between the radicals on the surface of the implant and the mediator molecules, the surface of the implant is first hydrophilized by applying a hydrophilic coating, in a further step the hydrophobic radicals on the surface modified in this way are then immobilized and then the mediator molecules are added to the surface for the noncovalent hydrophobic interaction with the radicals, the ratios of chain length and degree of occupation indicated above preferably being used for BMP-2.

The process according to the invention for the immobilization of the mediator molecules is distinguished in that the implant material employed consists of metallic materials such as pure titanium or metallic titanium alloys such as chromium/nickel/aluminum/vanadium/cobalt alloys (e.g. TiAlV4, TiAlFe2.5), stainless steels (e.g. V2A, V4A, chrome nickel 316L) or ceramic materials such as hydroxyapatite, alumina or of a combination, in which, for example, metallic material is coated with ceramic material. Synthetic polymer materials are also suitable for use as implant material.

The invention also relates to therapeutically preventing or alleviating, by coating a coronary stent (length about 10 mm) with the aid of a biomolecule or of a mediator, e.g. BMP-2, the late complication restenosis, which is caused by a proliferation of vascular smooth muscle cells, in order thus to promote healing and compatibility.

According to the invention, the mediator molecules can be biomolecules which are advantageous for the biocompatibility of the implant, in that they counteract a possible rejection of the implant and/or promote the ingrowth of the implant.

Mediator molecules which can be used in the present process are preferably proteins promoting bone growth from the class consisting of the bone growth factors 'bone morphogenic proteins' or alternatively ubiquitin. Advantageously, for immobilization a protein of this class on its own, in combination with further members of this class or alternatively together with biomolecules such as proteins of other classes or low molecular weight hormones or alternatively antibiotics, can be employed for the improvement of immune defense. In this case, these molecules can also be immobilized on the surface by means of bonds which can be cleaved in the biological medium.

According to the invention, the surface of the implant material is preferably chemically activated, the activation taking place by means of a silane derivative such as, for example, -aminopropyltriethoxysilane or a trimethyl-methoxy- or trimethylchlorosilane derivative or 3-glycidoxypropyltrimethoxysilane and the reaction being carried out both in an aqueous solvent and in an organic solvent. In a second step, mediator molecules can be immobilized on the implant material by means of noncovalent bonding to the surface activated in this way.

The process is characterized in that for the hydrophobic interaction the stationary insoluble phase used is a carrier on which a monomolecular, entropically ordered water structure is formed on apolar groups arranged gridlike situated thereon. A similar ordered monomolecular water layer is present on the hydrophobic areas of the protein (BMP). If the two molecules (e.g. alkyl radicals and BMP-2) come into contact with one another with their monomolecular water layers, the water layers are destroyed by a more unordered system of individual water molecules becoming of the ordered water structure. The free energy of the interaction thus results due to an increase in the entropy of the water molecules. At relatively high temperature, these hydrophobic interactions become stronger (greater free energy).

The BMP must be brought to hydrophobic interaction with a suitable hydrophobic carrier. Such a carrier consists, for example, of an insoluble phase and hydrophilic and hydrophobic chemical structures situated thereon. In particular, suitable carriers are all solid phases having hydrophilic surfaces which carry additional hydrophobic/apolar groups.

Specific examples for such carriers of organic and inorganic type are celluloses, agaroses or appropriate polymer particles coated with carbohydrates or polyhydroxycarbon chains, i.e. hydrophilically, and silica, zeolite or aluminum hydroxide particles.

Novel carriers are hydrophilic metal surfaces which are occupied/substituted gridwise appropriately with alkyl or aryl groups, for example, in a later process. On such solid phases, suitable degrees of substitution with hydrophobic groups lie in a range from 0.01 to 3.0 nmol/cm$^2$, preferably in a range from 0.01 to 2.0 nmol/cm$^2$, where the ratios indicated above should be kept to, in particular when using BMP-2.

A hydrophilic solid phase suitable for substitution with hydrophobic groups is preferably metal surfaces cleaned in dilute acid or metal surfaces enhanced using chromosulfuric acid having contact angles of between 0-90°, preferably 0-20°. In particular, suitable hydrophobically interacting metal surfaces cleaned with dilute acid are those such as titanium, steel, steel alloys such as Cr/Mo steel or steel or titanium surfaces enhanced using chromosulfuric acid, which has been substituted with methyl, ethyl, propyl, butyl, pentyl, hexyl, octyl, decyl, dodecyl or hexadecyl groups (chain length 1-30, preferably 1-20, particularly preferably 1 to 8 carbon atoms, preferably in a chain, which can also be substituted by one or more substituents such as methyl, ethyl, methoxy or ethoxy groups or halogen atoms such as chlorine, fluorine). The hydrophobic alkyl interaction can be strengthened by combination with a sulfur atom, for example in the form of a thioether bond or as a thiol such as (mercaptopropyl radicals).

Particular forms of hydrophobic interaction can also be achieved using immobilized aromatic radicals (phenyl or tolyl radicals, 6-7 C atoms), in particular in combination with sulfur atoms (phenylthiosilane, or thienyl radicals, 4-6 C atoms).

The hydrophobic interaction at the contact sites takes place at temperatures from 0°-100° C., preferably at 5-50° C. at a pH of 3.0-11.0, preferably at pH 6-10. Preferably suitable degrees of substitution with the radicals are 0.1-2.5 nmol/cm$^2$, which corresponds to a lattice distance of the alkyl or aryl groups covalently coupled on the surface of 0.2-5 nm, preferably 0.3-1 nm.

With a molecule of 5-6 nm diameter, for example of BMP-2, at high degrees of substitution and thus small lattice distances (0.2-1 nm), a number of such radicals could react with the molecule and bond it firmly. The bonding strength (affinity) of the surface is thus proportional to the chain length of the alkyl radical and the degree of substitution and increases greatly with these parameters. A preferable bonding of BMP-2 takes place from a chain length of C–1, preferably C–3 (propyl) with a degree of substitution of 0.01-2.5 nmol/cm$^2$, preferably of 0.2-1 nmol/cm$^2$. With shorter alkyl chains, higher degrees of substitution, and with longer chains, lower degrees of substitution are preferred as minimum sizes.

Suitable substances for the synthesis of alkyl- or aryl-loaded metal surfaces are alkyltrichlorosilanes (methyltrichlorosilane, ethyltrichlorosilane, propyl-trichlorosilane, etc.), dialkyldichlorosilanes (di-methyldichlorosilane, diethyldichlorosilane, dipropyl-dichlorosilane etc.), trialkylchlorosilanes (trimethyl-chlorosilane, ethyldimethylchlorosilane, propyl- etc.), alkyltrimethoxysilanes, methyltrimethoxysilane, ethyl-, propyl- etc.), alkyltriethoxysilanes (methyltriethoxy-silane, ethyl-, propyl- etc.), phenyltrichlorosilane, phenyldimethylchlorosilane, phenylthiotrimethylsilane, p-tolyltrichlorosilane.

Continuing investigations of the inventors have shown that the anchoring of the alkyl or aryl radicals to the surface of the implant material can be improved qualitatively and quantitatively by providing on the implant surface a hydrophilic coating, for example agarose, polyacrylate, or preferably by increasing the number of metal oxide units available on the surface.

On the part of the inventors, it has been found that the number of oxide groups can surprisingly be increased by treating the surface of the metal with hot, preferably sediment-free, chromosulfuric acid. In contrast to the expectation that the metal dissolves under these conditions, when using this acid a novel essentially uniform hydrophilic oxide layer 5-50 nm thick is produced on the surface of the metal. The process is so gentle that even coronary stents (which can be manufactured, for example, from stainless steel or titanium) can be coated without destruction of the thin sensitive lattice work (50-150 m diameter). In the case of large implants, the hydrophilic oxide layer can achieve a thickness of 10 m up to 100 m and can be built up relatively "smoothly" without hollows or holes. The metal employed for the implant can in this case be pure titanium or titanium alloys (e.g. TiAlV4, TiAlFe2.5), aluminum or stainless steel (e.g. V2A, V4A, chrome nickel 316L, Cr/Mo steel). A commercially available chromosulfuric acid containing 92% by weight of $H_2SO_4$, 1.33% by weight of $CrO_3$ and having a density of 1.8 g/cm$^3$, obtainable, for example, from Merck, is preferably used to achieve a thin smooth layer of metal oxide. For this, the metal substrate is inserted into the chromosulfuric acid and treated for a period of 1 up to 3 hours at 100 to 250° C., preferably for 30 to 60 minutes at 240° C., then carefully rinsed with water, then boiled for 30 min in water or a solution of 1-4% EDTA (ethylenediamine tetraacetate) pH 7.0, preferably 2% EDTA pH 7.0, in order to remove heavy metal ions, e.g. chromium ions, remaining on the surface and then dried.

If a thicker metal oxide layer is to be provided on the metal surface and/or preferably an oxide layer having small micro- and nanopores, the chromosulfuric acid described above is diluted with water to a density of 1.5 to 1.6 g/cm$^3$. In a subsequently following treatment of the metal implant surface as described above with the acid diluted in this way, a "rough" surface layer having hollows and pores is formed, such that the surface available for loading with mediator molecules is enlarged. By adjustment of different densities of chromosulfuric acid and different treatment times and temperatures, it is therefore possible to apply a multiplicity of various oxide layers of different properties to metal surfaces with high adhesiveness. The invention is therefore also directed at such a process for the formation of a thermodynamically uniform metal oxide layer (no contact angle hysteresis) on the implant material by means of hot chromosulfuric acid.

The metal oxide layer on the implant material of the above-mentioned materials can then be activated by means of treatment with dilute nitric acid (about 5% by weight) and subsequent coupling of a silane derivative.

The mediator molecules can then be anchored noncovalently to the implant surface via the molecules of the silane derivative.

The implant material used can also be a ceramic material such as, for example, hydroxyapatite. The hydroxyapatite should in this case first be activated by treatment with aminoalkylsilane and the anchor molecules should then be anchored. According to the invention, anchor molecules are to be understood as meaning those molecules which are anchored to the surface of the implant and show noncovalent interactions with the mediator molecules if in the next step a noncovalent bonding of the mediator molecules, such as BMP, to the surface takes place.

If, under the coupling conditions, the mediators employed are poorly soluble in the medium, the solubility can be increased by addition of surfactants/detergents and the reaction can be carried out. Thus, at pHs of >6, poorly soluble bone growth factors and other mediators can be kept in solution by ionic or nonionic detergents in the concentration range 0.05-10%, preferably 1-5%, by weight, in particular in 0.066% SDS and pHs of >6, in particular at pH 8-10 for noncovalent bonding processes in the alkaline pH range without loss of the biological activity.

The influence of the materials modified by the process according to the invention on bone cells was investigated in animal experiments, the modified materials for this purpose having been prepared in platelet or dumbbell form. It was observed here that 4 weeks after the incorporation into the animals accelerated bone formation with contact to the implant surface by BMP-2 occurred on the materials.

The present invention is illustrated further with the aid of the following examples.

Modification of Metals (Titanium, 316 L Stainless Steel):

Either mechanically polished/electropolished, anodic-ally oxidized small titanium plates or small titanium alloy plates plasma-sprayed with porous titanium alloy with or without chromosulfuric acid enhancement are employed. To the same extent, stainless mechanically polished/electropolished steels with or without chromosulfuric acid enhancement can be employed.

Cleaning Processes

Before each use, the metals are cleaned by heating to 80° C. in 5% $HNO_3$ for 2 hours. After washing again in water, the small plates were dried by washing in 30 ml of dry methanol. Afterwards, they were either used directly or enhanced with chromosulfuric acid.

Chromosulfuric Acid Enhancement

In the chromosulfuric acid enhancement, the small titanium plates were incubated in chromosulfuric acid (92% $H_2SO_4$, 1.35 $CrO_3$) at 190-240° C. for 30-90 min and the small steel plates at 190-230° C. for 30-90 min. Afterwards, the metal samples were washed copiously with water and then boiled in 2% EDTA pH 7.0 and subsequently in water for 30 min in each case. After washing again in water, the small plates were dried by washing in 30 ml of dry methanol.

Loading of Surfaces with Aminopropyltriethoxysilane:

The cleaned carriers (5-10 small titanium plates) were treated under inert gas with or without chromosulfuric acid enhancement with 47.5 ml of toluene and 2.5 ml of aminopropyltriethoxysilane in a Teflon holder and sealed. The batch was then boiled under reflux and with slow stirring for 3-3.5 hours. The small plates were then washed 3 times with 10 ml of trichloromethane, acetone and methanol and then air-dried. At the aminopropyltriethoxysilane concentration indicated, it was possible with the aid of the Bolton-Hunter method to determine a surface concentration of amino groups of 1.5 to 2.5 nmol/cm$^2$.

Loading of Surfaces with Trialkylmonochlorosilanes:

The cleaned carriers (small metal plates) were treated with or without chromosulfuric acid enhancement with a 5% strength trialkylsilane solution (v/V) in dry toluene which additionally contains 5% of pyridine (v/v) with or without chromosulfuric acid enhancement. After a reaction time of 1-3 h, they are washed with ethanol, 0.01 M hydrochloric acid and dist. water. If required, the carriers can be dried in vacuo at 60-110° C.

Loading of Surfaces with Alkyltrimethoxysilanes:

The cleaned carriers (small metal plates) were treated with or without chromosulfuric acid enhancement with a 5% strength solution of alkyltrimethoxysilane solution (v/V) in dry trichloroethylene. After a reaction time of 12 h at room temperature, they are washed with trichloroethylene, acetone and ethanol. In the case of mercaptopropyltrimethoxysilane, UV light must be excluded. If required, the carriers (without SH groups) can be dried in vacuo at 100-110°.

Loading of Surfaces with Dichlorodialkyl- and Tri-Chloroalkylsilanes:

The cleaned carriers (small metal plates) were treated in dry toluene with or without chromosulfuric acid enhancement with a 5-10% strength dichlorodialkyl- or trichloroalkylsilane solution (v/V). After a reaction time of 1-3 h, they are washed with ethanol and dist. water. If required, the carriers can be dried in vacuo at 60-110° C.

Binding of rhBMP-2 to a Propylamine-titanium Binding Lattice:

The propylamine-coated small titanium plates were washed with 125 mM Na borate buffer, 0.066% sodium dodecyl sulfate, pH 10.0 and equilibrated. They were then treated with an rhBMP-2 solution (recombinant human BMP-2) (0.2-0.3 mg/ml in 125 mM Na borate buffer, 0.066% sodium dodecyl sulfate, pH 10.0) and incubated with shaking at room temperature for 12-14 hours. They were then washed 4× with borate buffer and subsequently with water.

Binding of rhBMP-2 to electropolished titanium: 10-30 ng/cm$^2$

Binding of rhBMP-2 to chromosulfuric acid-enhanced titanium: 2-10 ng/cm$^2$

Binding of rhBMP-2 to chromosulfuric acid-enhanced propylamine-titanium binding lattice: 100-270 ng/cm$^2$ Similarly high values can also be obtained for chromosulfuric acid-enhanced titanium with a clean propyltitanium binding lattice. It is to be observed here that the hydrophobically adsorbed BMP-2, however, cannot be washed off by extensive washing with buffer solutions or water.

As indicated above, surprisingly the noncovalently bonded loading with BMP-2 was also not able to be removed by use of a surfactant such as with a 1% SDS solution, which allows it to be concluded that there are extremely strong adsorption forces. These hydrophobic interactions can be strengthened by charge transfer complexes, H bond formation and charge weakening, while substitution of the chain with hydroxyl or thiol groups and charge strengthening by, for example, ammonium radicals leads to the weakening of the hydrophobic interactions.

In this case, the inventors found in their experiments that a controlled release of BMP-2 can be decisively influenced by a positive charge present on the alkyl radical. In this case, the pK of the alkaline group —NH$_2$ plays an important role, which can lie at pK 8-12 and can be strongly influenced by substitution of the nitrogen, for example to give the quaternary ammonium ion, such that a charge-influenced adsorption dependent on the pH and later release of the BMP-2 on the surface take place.

Even at a pH of 7.0, in the physiological range, the noncovalent bond between the hydrophobic ligands immobilized on the metal and the BMP-2 is extraordinarily stable, such that at most 0.1-1% of the adsorbed BMP is released per day. Since in the case of groups substituted with amino groups on the implant surface both the amino groups and the BMP are positively charged at a pH of 7.0, an electrostatic adsorption is virtually excluded in this case.

The experiments described above were carried out under appropriately adjusted conditions using the other compounds included in the table. These are mean values of in each case 4 experiments with standard deviation. The small plates (5×10×1 mm; =1 cm$^2$), after pre-cleaning with HNO$_3$ or after pretreatment with chromosulfuric acid, were individually washed 4× in 125 mM borate, 0.066% SDS, pH 10, for 15 min. The adsorption conditions were as follows: $^{125}$I-BMP-2 solution: $C_{bmp}$=0.1 mg/ml in 125 mM borate, 0.066% SDS, pH 10; 12-14 h at 5° C.

The abbreviations used in the table have the following meaning:

Ti-EP: electropolished metal
Ti-CSB: metal treated with chromosulfuric acid
v: advance angle (peripheral angle measurement according to Wilhelmy)
R: withdrawal angle (peripheral angle measurement according to Wilhelmy)
$t_{1/2}$: half-life of the release of $^{125}$I-rhBMP-2

TABLE

| | Noncovalent immobilization of rhBMP-2 on alkyl-, fluoroalkyl-, phenyl-, and fluorophenyl- modified titanium surfaces | | | | | | | |
|---|---|---|---|---|---|---|---|---|
| | Silanizing agent | Titanium (electropolished) ng/cm$^2$ | Titanium chromosulfuric acid-treated ng/cm$^2$ | Ti-EP $V_1^a$ | Ti-EP $R_1^a$ | Ti-CSB $V_1^a$ | Ti-CSB $R_1^a$ | Ti-EP $T_{1/2}$ (days) |
| 1 | Ti control 1 (nonspecific adsorption) | 29 ± 4 | 2 ± 2 | 40 | 17 | 0 | 0 | |
| | | | | 34 | 12 | 3 | 4 | |
| | | | | 33 | 16 | 0 | 3 | |
| | | | | 48 | 8 | 0 | 0 | |
| | | | | 40 | 12 | | | |
| 2 | H$_2$NCH$_2$CH$_2$CH$_2$Si(OC$_2$H$_5$)$_3$ C$_9$H$_{23}$NO$_3$Si aminopropyltriethoxysilane (APS) | 21 ± 2 | 105 ± 14 | 87 | 19 | 87 | 29 | 67 |
| | | | | 86 | 18 | 87 | 31 | |

TABLE-continued

Noncovalent immobilization of rhBMP-2 on alkyl-, fluoroalkyl-, phenyl-, and fluorophenyl- modified titanium surfaces

| | Silanizing agent | Titanium (electropolished) ng/cm² | Titanium chromosulfuric acid-treated ng/cm² | Ti-EP $V_1^a$ | Ti-EP $R_1^a$ | Ti-CSB $V_1^a$ | Ti-CSB $R_1^a$ | Ti-EP $T_{1/2}$ (days) |
|---|---|---|---|---|---|---|---|---|
| 3 | 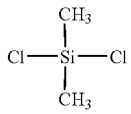 C₂H₆Cl₂Si dimethyldichlorosilane (DDS) | 69 ± 29 | 228 ± 16 | 77<br>87 | 58<br>52 | 89<br>87 | 47<br>48 | 100 |
| 4 | 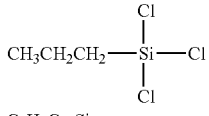 C₃H₇Cl₃Si n-propyltrichlorosilane (PTC) | 71 ± 5 | 121 ± 25 | 87<br>87 | 53<br>56 | 86<br>87 | 60<br>61 | |
| 5 | 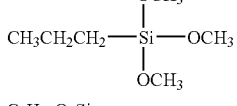 C₆H₁₆O₃Si propyltrimethoxysilane (PTM) | 68 ± 10 | 121 ± 27 | 81<br>85 | 22<br>18 | 88<br>86 | 23<br>25 | |
| 6 | 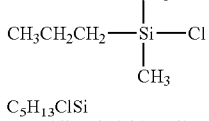 C₅H₁₃ClSi propyldimethylchlorosilane (PDMC) | 43 ± 2 | 68 ± 10 | 87<br>84 | 33<br>7 | 39<br>38 | 1<br>2 | |
| 7 | 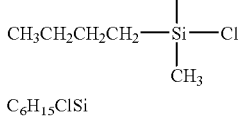 C₆H₁₅ClSi n-butyldimethylchloro-silane (BDMC) | 31 ± 2 | 64 ± 3 | 72<br>70 | 12<br>4 | 74<br>75 | 4<br>5 | |
| 8 | 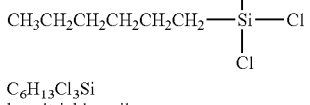 C₆H₁₃Cl₃Si hexyltrichlorosilane (HTC) | 81 ± 8 | 218 ± 16 | 87<br>87 | 7<br>13 | 63<br>54 | 6<br>0 | 96 |
| K | Ti control 2 (nonspecific adsorption) | 15 ± 3 | 5 ± 1 | | | | | |
| 9 | 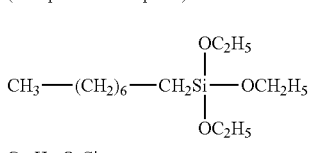 C₁₄H₃₂O₃Si n-octyltriethoxysilane (C8) | 59 ± 2 | 119 ± 31 | 85<br>87 | 38<br>37 | 57<br>52 | 1<br>6 | |

TABLE-continued

Noncovalent immobilization of rhBMP-2 on alkyl-, fluoroalkyl-, phenyl-, and fluorophenyl- modified titanium surfaces

| | Silanizing agent | Titanium (electropolished) ng/cm² | Titanium chromosulfuric acid-treated ng/cm² | Ti-EP $V_1{}^a$ | Ti-EP $R_1{}^a$ | Ti-CSB $V_1{}^a$ | Ti-CSB $R_1{}^a$ | Ti-EP $T_{1/2}$ (days) |
|---|---|---|---|---|---|---|---|---|
| 10 | $CH_3-(CH_2)_{10}-CH_2Si(OC_2H_5)_3$ <br> $C_{18}H_{40}O_3Si$ <br> n-dodecyltriethoxysilane (C12) | 25 ± 1 | 76 ± 7 | 86<br>87 | 61<br>60 | 72<br>73 | 8<br>9 | |
| 11 | $CH_3-(CH_2)_{10}-CH_2Si(OC_2H_5)_3$ <br> $C_{24}H_{52}O_3Si$ <br> n-octadecyltriethoxysilane (C18) | 14 ± 3 | 51 ± 11 | 87<br>87 | 60<br>60 | 87<br>86 | 57<br>32 | |
| 12 | $CF_3-(CF_2)_3-CH_2-CH_2-Si(OC_2H_5)_3$ <br> $C_{14}H_{19}F_{13}O_3Si$ <br> Tridecafluoro-1,1,2,2-tetrahydrooctyl)triethoxy-silane (F13) | 24 ± 4 | 62 ± 11 | 83<br>86 | 61<br>60 | 86<br>86 | 21<br>21 | |
| 13 | $CF_3-(CF_2)_3-CH_2-CH_2-Si(OC_2H_5)_3$ <br> $C_{16}H_{19}F_{17}O_3Si$ <br> (heptadecafluoro-1,1,2,2-tetrahydrodecyl)triethoxy-silane (F17) | 24 ± 7 | 57 ± 16 | 90<br>90 | 17<br>67 | 87<br>86 | 60<br>59 | |
| 14 | Phenyl-$Si(OC_2H_5)_3$ <br> $C_{12}H_{20}O_3Si$ <br> phenyltrriethoxysilane (Phe) | 44 ± 12 | 67 ± 20 | 54<br>52 | 15<br>12 | 43<br>35 | 12<br>7 | |
| 15 | Pentafluorophenyl-$CH_2-CH_2-CH_2-Si(OC_3)_3$ (actually $-Si(OCH_3)_3$) <br> $C_{12}H_{15}F_5Si$ <br> Pentafluorophenylpropyl-trimethoxysilane (5FPP) | 50 ± 7 | 105 ± 13 | 77<br>80 | 17<br>18 | 57<br>45 | 6<br>5 | |

The invention claimed is:

1. A method for treating a patient, comprising:
    implanting into the patient a metallic or ceramic bioactive implant device,
    wherein the device comprises:
    (a) anchor molecules covalently bound to a surface of the device, and
    (b) mediator proteins each of which forms at least four non-covalent hydrophobic interactions with hydrophobic radicals of the anchor proteins and no covalent interactions with the anchor molecules,
    wherein said bioactive implant device provides for release of biologically active mediator proteins under physiological conditions of implantation.

2. The method of claim 1, wherein the hydrophobic radicals of the anchor molecules have 1 to 30 carbon atoms, optionally replaced by silicon or heteroatoms such as N, O or S in the chain, wherein the hydrophobic radicals are optionally substituted by one or more substituents from halogen, alkoxy, hydroxyl, thiol, amino, alkyl-amino, dialkylamino or trialkylamino groups, and wherein alkyl groups of the substituents optionally have 1 to 6 carbon atoms and are straight-chain or branched.

3. The method of claim 1, wherein the hydrophobic radicals are branched carbon chains optionally substituted by one or more substituents from halogen, alkoxy, hydroxyl, thiol, amino, alkyl-amino, dialkylamino or trialkylamino groups, and wherein alkyl groups of the substituent optionally have 1 to 6 carbon atoms and are straight-chain or branched having 1 to 30 carbon atoms.

4. The method of claim 1, wherein the implant device comprises a material selected from the group consisting of metals, metallic alloys, and ceramic materials and combinations thereof.

5. The method of claim 1, wherein the mediator proteins are biologically active substances.

6. The method of claim 5, wherein the mediator proteins are BMP-2 or BMP-7.

7. The method of claim 1, wherein the the device further comprises a hydrophilic coating between the surface of the device and the anchor molecules.

8. The method of claim 7, wherein the hydrophilic coating is a hydrophilic oxide layer.

9. The method of claim 8 wherein the device comprises titanium, a titanium alloy, aluminum or stainless steel.

10. The method of claim 9 wherein the oxide layer is provided by treating the device with chromosulfuric acid for a period of 0.5 up to 3 hours at 100 to 250° C.

11. The method of claim 10, wherein the chromosulfuric acid has a density of 1.40 $g/cm^3$.

12. The method of claim 1, wherein the anchor molecules are straight-chain or branched, having 1 to 30 carbon atoms, optionally substituted by one or more substituents from halogen, alkoxy, hydroxyl, thiol, amino, alkyl or dialkylamino groups, and wherein the anchor molecules are arranged to not interact with one another.

13. The method of claim 1, wherein the device comprises at least 3 hydrophobic radicals of the anchor molecules per 10 $nm^2$ of the surface.

14. The method of claim 1, wherein the device comprises at most 100 hydrophobic radicals of the anchor molecules per 10 $nm^2$ of the surface.

15. The method of claim 1, wherein the device comprises a joint or bone prosthesis, a stent or dental implant device.

16. The method of claim 1, wherein the patient is treated for arthrodysplasia, joint luxation or a disease which can develop on the wear of joints as a result of malarticulation.

17. The method of claim 1, wherein said anchor molecules are arranged so as to not interact with one another.

18. The method of claim 1, wherein each mediator protein forms at least 10 non-covalent hydrophobic interactions with hydrophobic radicals of the anchor molecules.

19. A method for treating a patient, comprising:
 implanting into the patient a metallic or ceramic bioactive implant device comprising:
 (a) anchor molecules covalently bound to a surface of the device, and
 (b) mediator proteins each of which forms at least four non-covalent hydrophobic interactions with hydrophobic radicals of the anchor molecules,
 wherein said bioactive implant device provides for release of biologically active mediator proteins under physiological conditions of implantation.

20. The method of claim 19, wherein each mediator protein forms at least 10 non-covalent hydrophobic interactions with hydrophobic radicals of the anchor molecules.

\* \* \* \* \*